United States Patent [19]

Omura et al.

[11] 4,159,346
[45] Jun. 26, 1979

[54] TABLET COMPOSITIONS

[75] Inventors: Yukikazu Omura; Juno Uesugi; Kimihiko Takeo; Tooichiroo Hirano, all of Miyazaki, Japan

[73] Assignee: FMC Corporation, Philadelphia, Pa.

[21] Appl. No.: 823,059

[22] Filed: Aug. 9, 1977

[30] Foreign Application Priority Data

Sep. 7, 1976 [JP] Japan ................................ 51-106246

[51] Int. Cl.² ............................................. A61K 47/00
[52] U.S. Cl. ...................................... 424/362; 424/361
[58] Field of Search ................................. 424/361, 362

[56] References Cited

U.S. PATENT DOCUMENTS

| 3,146,168 | 8/1964 | Battista | 424/362 X |
| 3,332,848 | 7/1967 | Magid | 424/362 X |
| 3,622,677 | 11/1971 | Short et al. | 424/361 |
| 3,632,778 | 1/1972 | Sheth et al. | 424/361 X |
| 3,679,794 | 7/1972 | Bentholm et al. | 424/362 X |
| 3,852,421 | 12/1974 | Koyanagi et al. | 424/361 X |
| 3,966,899 | 6/1976 | Nakai et al. | 424/19 |
| 4,001,434 | 1/1977 | Nakai et al. | 424/361 |
| 4,017,598 | 4/1977 | Ohno et al. | 424/35 |

*Primary Examiner*—Shep K. Rose
*Attorney, Agent, or Firm*—Charles H. Johnson

[57] ABSTRACT

A pharmaceutical or other tablet containing a pharmacologically active ingredient in an amount of at least about 75% of the weight of the tablet is formed by a wet-granulation tableting process and involves the use by β-1,4 glucan powder and a particular specified binder.

3 Claims, No Drawings

TABLET COMPOSITIONS

This invention relates to wet granulation compositions in which β-1,4-glucan powder that is hereinafter defined is used. More specifically, this invention relates to compositions used for obtaining, by wet granulation tableting, tablets, which are frequently used among solid dosage forms such as powders, granules, tablets and capsules, the tablets having a high content of a drug or other active ingredient and being excellent in quality.

As the methods for forming tablets, there have heretofore been three types: the first one being a method of direct compression tableting comprising the two steps of powder-mixing and tableting: the second one being a method of dry granulation tableting comprising the steps of preliminarily compressing a mixed powder, crushing, sieving and tableting: and the third one being a method of wet granulation tableting which requires complicated steps of powder-mixing, kneading, granulation, drying, sieving, mixing and tableting. The last one is employed for the formulations with which direct compression tableting and dry granulation tableting are difficult.

With the development of tableting techniques, it has become possible to tablet formulations which have so far been believed to be difficult to tablet. However, many bad effects due to forcible and thoughtless tableting have recently been pointed out. Above all, names of drugs having been proved to be unsuitable from the viewpoint of medicinal effects often appear in newspapers, which are increasing uneasiness of people taking medicines.

As to the cause of such ineffectiveness of drugs, it has been reported that, in some cases, medicinal effects of an active ingredient itself are questionable. However, the inventors have now found that complicated wet granulation conditions are sometimes the cause of the ineffectiveness, and have accomplished the invention which can completely satisfy requirements for both of improvement in efficiency of manufacturing and dissolution rate (which is considered to have a parallel relation with efficacy in the case of water-soluble drugs), both of which are problems that drug manufacturers have now confronted.

The present invention will now be illustrated in more detail now.

Looking at the progress of wet granulation tableting, it was, up to recently, a pattern of improvement of efficiency that efficiency is increased by developing a granulator of higher performance. By the development of various granulators, the improvement in efficiency of wet granulating tableting has been advanced, and at present, the main point of the improvement of efficiency has been turned to miniaturization of tablets.

However, conventional investigations have predominantly been directed to the improvements of productivity and apparent qualities (e.g., hardness, weight variation, disintegration time, friability, etc.), which have lead to the ineffectiveness of medicinal effects or the like pointed out as described above.

The inventors paid attention to the problem of miniaturization of tablets as well as the problem of dissolution and continued developing and investigating manufacturing methods. As a result, we have succeeded in obtaining tablets containing more than 75% of a drug, irrespective of the type of the drug, which are excellent in both apparent quality and dissolution rate by combining the drug with β-1,4-glucan powder and one of three types of suitable binders in a suitable ratio.

The progress up to the achievement of this invention is described in more detail below. In carrying out the miniaturization of tablets, if the diameter of tablets is reduced without changing the composition of ingredients, it becomes satisfactorily easy to take medicine, but it is inevitable to increase the number of tablets to be administered per one time and to lower production capacity and increase cost. In order to make tablets containing the same amount of a drug, it is required to reduce the amounts of additives other than the drug, i.e., an excipient, a binder or the like. If simply the amounts of these are reduced and the diameter of tablets is minimized, hardness is, as a matter of course, remarkably lowered, thereby making tableting difficult.

In order to solve these problems, when microcrystalline cellulose (hereinafter referred to as MCC) of high compressibility is, for example, used in a large amount and the resulting tablet composition is made into tablets by the conventional wet granulation tableting method, a binder solution is required to be used in a large amount and a long drying time (or high drying temperature) is required because of the high water absorption of MCC. If the type and amount of the binder are not satisfactorily selected and, in addition, drying is intensified, hornification of MCC advances and, apart from tablet hardness, disintegration and dissolution rate are, therefore, inevitably deteriorated. The improvement only of disintegration could be attained by incorporating a disintegrating agent which is usually employed, but drug manufacturers have a common opinion that they are unwilling to use the disintegrating agent from the viewpoint of the stability and reactivity of drugs.

The inventors have minutely analyzed the effects of MCC, which is one example of β-1,4 glucan powder, considering the above-said actual circumstances. For using MCC of high compressibility most effectively in wet granulation tableting, kneading conditions are important. It is required that the particle size of MCC is reduced to 5 to 20 μ, preferably 6 to 12 μ, by attrition in kneading. When MCC having a particle size within this range is used in wet granulation tableting, MCC exhibits highest compressiblity and, therefore, the amount of an excipient added can be reduced to less than 10%.

Moreover, in order to satisfy requirements for all of the qualities of tablets obtained by the attrition of MCC into 5 to 20 μ by using a kneader which is frequently used and adjusting a kneading time (to 30 to 60 min.), followed by granulation and tableting, the combination with a binder is important.

As a result of investigations for finding out the most optimal binders to be used independently or in combination among gelatin, arabic gum, guar gum, locust bean gum, sodium alginate, carageenan, sodium carboxymethylcellulose (hereinafter abbreviated as CMC-Na), methyl cellulose (hereinafter abbreviated as MC), hydroxypropylstarch (hereinafter abbreviated as HPS), hydroxypropyl cellulose (hereinafter abbreviated as HPC), potato starch (hereinafter abbreviated as PS), corn starch, agar-agar, polyvinyl alcohol (hereinafter abbreviated as PVA), polyvinyl pyrrolidone (hereinafter abbreviated as PVP), etc., binders which satisfy all the requirements after tableting are found to be the three of HPS, PS and CMC-Na.

The binders, HPS, PS and CMC-Na, are incorporated alone (the partially combined use of them is possible) in amounts by weight, as a 3 to 10% aqueous solution, of 7 to 25 parts, 6 to 23 parts and 8 to 27 parts, respectively, to mixed powders consisting of 75 to 95 parts of a water-soluble drug and 5 to 25 parts of MCC. By adding such binder and kneading for 30 to 60 min by means of a kneader, a kneaded composition which contains MCC having a particle size of 5 to 20 μ can be obtained.

The above kneaded composition is granulated using a crushing granulator. The obtained granulations are dried at 40° C. for 4 to 8 hours using a hot-air dryer. The resulting dry granules have such a particle size that more than 99% of them pass through a sieve of 12 mesh. To the granules, a lubricant such as stearic acid (hereinafter referred to as St) is added and, then, tableting is carried out with a compression pressure being changed to obtain small tablets having excellent qualities which have a diameter of 5 mm and weight 50 mg per tablet. It has already been confirmed that, as a matter of course, granulations which are made using other types of granulation also provide tablets having the same qualities.

The effects of this invention can be equally obtained even when $\beta$-1,4-glucan powders other than MCC are used. In this case, $\beta$-1,4-glucan powder other than MCC requires a kneading time about twice as long as the optimum kneading time in the case of using MCC, since $\beta$-1,4-glucan powder particles are difficult to be loosened in kneading.

$\beta$-1,4 glucan powder referred to in the present invention is prepared from a starting material of cellulose, containing active ingredients of plants, through chemical decomposition, mechanical decomposition or irradiation with ultrasonic waves or with high energy electron beam. The chemical decomposition may be conducted according to any known process. The mechanical grinding may be conducted in either a dry process or a wet process, freely using a ball mill, a hammer mill, a tube mill, a vibration mill, or other types of mills or crushers. As the process of grinding cellulose materials by using ultrasonic waves or irradiating with high energy electron beams, there are, for example, the process described in *Textile Research Journal,* August, pp. 549–553 (1950) by F. M. Morehead, or the process described in *Journal of Textile Society,* vol. 15, No. 11 (1959) by Imamura, Minakami, et al., which, however, are not limitative at all.

Moreover, it is desired that $\beta$-1,4-glucan powders of this invention entirely pass through a sieve of 50 mesh (300 μ). If this invention is carried out using coarse $\beta$-1,4-glucan powders which do not pass through a 50 mesh sieve, the resulting tablets tend to cause capping, lamination or sticking and exhibit prolonged disintegration time and, further, tablet hardness obtained becomes low. This is because attrition effect is poor in kneading and, therefore, $\beta$-1,4-glucan particles do not come to form uniform and satisfactory network in the tablet matrix.

It will be apparent that this invention based on the finding of the composition which comprises such an amount of $\beta$-1,4-glucan powder, e.g., MCC, and such a type and amount of a binder as is matched to kneading by means of a kneader which is frequently used greatly contributes to the technical innovation of wet granulation tableting.

Examples will be described hereinafter for further understanding of the present invention. However, describing the examples, process of the examples or the like are partly outlined below.

There exist many water-soluble drugs and other pharmocologically active materials. Of them, sodium salicylate, caffeine sodium benzoate, vitamin $B_1$, vitamin $B_6$, ascorbic acid (hereinafter abbreviated as VC), aminopyrin, ephedrine hydrochloride, aminophylline, etc. were used for the investigations. However, since almost the same tendency was observed from the viewpoint of tablet qualities, the inventors have concluded that the present invention is applicable to other water-soluble drugs as well. Examples are given with respect to the system of using VC which is quite often used and which can be determined even in a slight amount through ultraviolet ray absorbance.

Additionally, the method of measuring tablet qualities are explained below.

(1) Tablet hardness:

A load was applied to the tablet sides using a KIYA type hardness tester to measure a load (kg) at break. The tablet hardness was indicated in terms of the load at break, (Average values of n=20)

(2) Disintegration time:

This measurement was conducted using a disintegration time tester meeting the standard of Japanese Pharmacopoeia. As a disintegrating solution, pure water of 37°±2° C. was used. Average values of n=6 were employed.

(3) Weight variation of tablets:

Tablets were weighed one by one using a chemical balance (Mettler). Standard deviation of n=20 was divided by average weight, then multiplied by 100. The results were used for indicating the weight variation of tablets.

(4) Measurement of the active ingredient content:

20 Tablets were ground, and 3 g of the thus obtained powder was used. The active ingredient content was measured according to the method described in Japanese Pharmacopoeia.

(5) Dissolution test:

This test was conducted according to the rotary basket method of United States Pharmacopoeia. 500 ml of a dissolution medium (first solution for dissolution test prescribed in Japanese Pharmacopoeia: pH 1.2) was poured into a 1 liter beaker and, while maintaining the solution temperature at 37° C., one tablet was placed in a basket and rotated at 150 RPM. 2 ml of the sample solution was taken out at definite time intervals with a whole pipet using a membrane filter as a filter material. After adding thereto 25 ml of the first solution, pure water was added to make the total 100 ml. Absorbance at a wavelength of 245 nm was measured using a spectrophotometer. Dissolution amount was determined according to a calibration curve method. (dissolution ratio was indicated in terms of percentage to the amount of contained active ingredient.)

EXAMPLE 1

After adding 5–25 parts of 2–12% potato starch solution to a mixture of 90 parts of vitamine C and 10 parts of MCC, the mixture was kneaded together for 15–90 minutes with a kneader and part of the mixture was picked up. After dissolving its soluble substance in warm water, it was filtrated with a glass filter and the residues (MCC) were dispersed again in water. After measurement of particle size by transillumination, kneading, granulation, drying and sieving, it was subject to tableting with the addition of 0.5% Mg-St as lubricant. Measurements of the tablet hardness and the results of the disintegration test are given in Table 1.

Table I

| PS conc. | Amt. added | Strength (kg) compression force*: 600kg/cm$^2$ | Disintegration (min.) Compression force:600kg/cm$^2$ | Avg. particle size ($\mu$) for MCC in paste | | | | |
|---|---|---|---|---|---|---|---|---|
| | | | | 15 min | 30 min | 45 min | 60 min | 90 min |
| 2% | 5 | 3.4 | 0.4 | 36 | 34 | 32 | 31 | 30 |
| | 12.5 | 4.1 | 0.7 | 33 | 27 | 23 | 21 | 20 |
| | 20 | 4.6 | 6.7 | 34 | 27 | 22 | 19 | 17 |
| | 25 | 4.3 | 35.0 | 37 | 34 | 30 | 25 | 19 |
| 7% | 5 | 4.2 | 0.8 | 35 | 33 | 32 | 32 | 31 |
| | 12.5 | 7.5 | 1.5 | 30 | 22 | 14 | 10 | 8 |
| | 20 | 8.9 | 25.5 | 28 | 16 | 10 | 6 | 4 |
| | 25 | 8.0 | over 60 | 32 | 25 | 18 | 11 | 3 |
| 12% | 5 | 4.9 | 0.8 | 35 | 33 | 32 | 32 | 31 |
| | 12.5 | 7.2 | 4.3 | 33 | 26 | 22 | 19 | 15 |
| | 20 | 8.6 | 50.0 | 26 | 16 | 11 | 8 | 6 |
| | 25 | 7.9 | over 60 | 30 | 26 | 20 | 16 | 9 |

*60-minute paste is used for granulation.

EXAMPLE 2

5% binders were added to a mixture powder consisting of 90 parts of VC and 10 parts of β-1,4-glucan of 45 μ in average particle size with changing the kind and the amount of the binders. After granulation, drying and sieving, the mixture was tableted to conduct tablet hardness test, disintegration time test and dissolution time test. The results are shown in Table 2.

Additionally with respect to the binders, since it was found as a result of extensive investigations that natural gum, sodium alginate, carageenan and the like are inferior to gelatin in all of hardness after tableting, disintegration time and dissolution time, data are tabulated in Table 2 mainly listing systems excellent in tablet qualities.

EXAMPLE 3

60-20 Parts of a mixture of lactose (DMV-200) and corn starch (4:1), both being popular conventional excipients for wet granulation tableting, was added to 40-80 parts of VC, and 17 parts of a 5% PS aqueous solution was added to the resulting mixture powder, then kneaded. After granulating using a flash mill, the mixture was dried and sieved. Then a lubricant, St., was added in a content of 0.5% and mixed, followed by tableting into 200 mg tablets and 100 mg tablets at a compression force of 600 kg/cm$^2$ using 8 mm diameter 12R and 6 mm diameter 12R punches and dies, respectively. At the same time, 17 parts of a 5% PS aqueous solution was added to a mixture powder consisting of 90 parts of VC and 10 parts of MCC, and tableted under the same condition as with the lactose system to measure tablet hardness. As is clear from Table 3, it is im- Table 2

| Name | Amount | Hardness (Kg) Compression Force (600 kg/cm$^2$) | Disintegration Time (min), Compression Force (600 kg/cm$^2$) | Dissolution rate (%) | | |
|---|---|---|---|---|---|---|
| | | | | After 5 min. | After 30 min. | After 60 min. |
| PS | 5 | 4.1 | 0.9 | 100.0 | 100.0 | 100.0 |
| | 10 | 6.8 | 1.3 | " | " | " |
| | 15 | 7.9 | 4.0 | 98.9 | 99.2 | 99.2 |
| | 20 | 8.7 | 24.2 | 41.2 | 87.2 | 98.0 |
| | 25 | 8.1 | more than 65 | 6.3 | 39.4 | 65.3 |
| HPC | 5 | 4.9 | 3.7 | 78.3 | 94.7 | 99.6 |
| | 10 | 7.1 | 23 | 37.7 | 78.0 | 97.6 |
| | 15 | 8.2 | 44 | 29.2 | 60.2 | 83.0 |
| | 20 | 8.5 | 62 | 18.9 | 45.1 | 63.0 |
| | 25 | 10.9 | more than 65 | 3.4 | 23.0 | 49.0 |
| CMC-Na | 5 | 5.0 | 0.5 | 100.2 | 100.2 | 100.2 |
| | 10 | 7.4 | 0.8 | 100.4 | 100.4 | 100.4 |
| | 15 | 7.9 | 6.3 | 76.3 | 99.8 | 99.8 |
| | 20 | 8.2 | 28.3 | 26.8 | 86.9 | 96.3 |
| | 25 | 8.8 | 63.0 | 17.5 | 43.8 | 64.6 |
| HPS | 5 | 4.7 | 1.6 | 100.0 | 100.0 | 100.0 |
| | 10 | 6.8 | 1.2 | 101.0 | 101.0 | 101.0 |
| | 15 | 7.5 | 6.0 | 100.1 | 100.1 | 100.1 |
| | 20 | 8.4 | more than 65 | 39.5 | 83.7 | 96.6 |
| | 25 | 9.6 | more than 65 | 15.9 | 63.4 | 81.0 |
| PVA | 5 | 3.9 | 3.9 | 64.3 | 91.4 | 98.4 |
| | 10 | 5.8 | 35.0 | 25.2 | 53.0 | 79.2 |
| | 15 | 6.7 | more than 65 | 6.3 | 25.1 | 46.9 |
| | 20 | 7.3 | more than 65 | 2.7 | 18.4 | 32.3 |
| | 25 | 7.0 | more than 65 | 1.9 | 10.8 | 23.1 |
| Gelatin | 5 | 4.0 | 1.9 | 72.0 | 98.8 | 98.8 |
| | 10 | 6.5 | 26.0 | 13.0 | 40.0 | 72.0 |
| | 15 | 7.3 | more than 65 | 7.7 | 21.1 | 39.6 |
| | 20 | 7.2 | more than 65 | 3.1 | 13.9 | 27.0 |
| | 25 | 6.5 | more than 65 | 1.8 | 11.4 | 22.9 | possible to reduce the tablet size by 50% (with the same content of the active ingredient) through the conventional process, whereas the present invention enables it to be realized with ease.

Additionally, with the formulations using lactone and corn starch as excipients, the most optimal amount of the binder is 15–18 parts by weight of the tablet which is accidentally analogous to that of MCC system. However, the allowance range thereof is extremely narrow.

Table 3

| Excipient | | Tablet Diameter 8 mm 12 R 200 mg/Tablet | | | Tablet Diameter 6 mm 12R 100 mg/Tablet | | |
|---|---|---|---|---|---|---|---|
| Name | Amount | Hardness (kg) | Content of Drug (mg) | Weight Variation | Hardness (kg) | Content of Drug (mg) | Weight Variation |
| Lactose: Corn Starch = 4:1 | 60 | 9.4 | 79.3 | 1.2 | 6.8 | 39.7 | 1.6 |
| | 40 | 7.9 | 119.0 | 0.9 | 5.2 | 59.5 | 1.1 |
| | 30 | 4.8 | 138.8 | 1.3 | 3.0 | 69.4 | 1.5 |
| | 20 | 2.2 | 158.7 | 1.7 | 1.4 | 79.3 | 2.2 |
| MCC | 10 | 8.5 | 178.4 | 0.7 | 7.0 | 89.2 | 1.0 |

The effects of this invention are as so far described. While major efforts are now concentrated on the rationalization of pharmaceutical production and the re-examination of medicine effects, the paste of 6–12 $\mu$ particle sizes at which level MCC provides the highest compressing ability can be obtained by kneading together a known excipient of only 10% MCC and a known binder of HPS/PS/CMC-Na mixed at proper concentralization. In addition, this invention not only enables increased tablet hardness and reduced tablet diameter but also improves the disintegration time and dissolution rate of tablets without disintegration agent, which under the conventional method was impossible because binders were not commonly used and because proper binders could not be selected.

Having thus described the invention, what is claimed is:

1. The method of making a tablet containing at least about 75% by weight of a pharmacologically active ingredient comprising mixing a water-soluble pharmologically active material with beta-1,4 glucan powder, kneading the mixture to such extent as to reduce the particle size of the beta-1,4 glucan powder to 5 to 20 microns, adding to the mixture an aqueous solution of a water-soluble binder consisting of one or more materials selected from the class consisting of hydroxypropyl starch, potato starch and sodium carboxymethylcellulose, and forming said materials into a tablet by a known wet-granulation tableting process.

2. The method set forth in claim 1 wherein the aqueous solution of the water-soluble binder is a 3% to 10% solution.

3. A tablet made in accordance with the method of claim 1.

* * * * *